United States Patent
Wang et al.

(10) Patent No.: US 11,298,220 B2
(45) Date of Patent: Apr. 12, 2022

(54) BREAST TREATMENT DEVICE

(71) Applicant: LifeCell Corporation, Madison, NJ (US)

(72) Inventors: Kai-Roy Wang, Jersey City, NJ (US); Sangwook Park, Virginia Beach, VA (US)

(73) Assignee: LifeCell Corporation, Madison, NJ (US)

( * ) Notice: Subject to any disclaimer, the term of this patent is extended or adjusted under 35 U.S.C. 154(b) by 57 days.

(21) Appl. No.: 16/864,670

(22) Filed: May 1, 2020

(65) Prior Publication Data

US 2020/0345476 A1 Nov. 5, 2020

Related U.S. Application Data (60) Provisional application No. 62/842,915, filed on May 3, 2019.

(51) Int. Cl.
*A61F 2/12* (2006.01)
*A61F 2/00* (2006.01)

(52) U.S. Cl.
CPC .............. *A61F 2/12* (2013.01); *A61F 2/0063* (2013.01); *A61F 2230/0071* (2013.01); *A61F 2240/001* (2013.01); *A61F 2310/00005* (2013.01)

(58) Field of Classification Search
CPC ........................................................ A61F 2/12
USPC ........................................................ 623/7–8
See application file for complete search history.

(56) References Cited

U.S. PATENT DOCUMENTS

| | | | |
|---|---|---|---|
| 2,108,205 | A | 2/1938 | Martin |
| 3,683,424 | A | 8/1972 | Pangman |
| 3,744,094 | A | 7/1973 | Bach |
| 4,298,998 | A | 11/1981 | Naficy |
| 4,840,629 | A | 6/1989 | Bustos |
| 4,936,858 | A | 6/1990 | O'Keeffe |
| 4,984,585 | A | 1/1991 | Austad |
| 5,066,303 | A | 11/1991 | Bark et al. |
| 5,352,307 | A | 10/1994 | Wild |
| 5,356,429 | A | 10/1994 | Seare |
| 5,447,535 | A | 9/1995 | Muller |
| 5,584,884 | A | 12/1996 | Pignataro |
| 5,658,328 | A | 8/1997 | Johnson et al. |
| 5,658,330 | A | 8/1997 | Carlisle et al. |
| 5,676,161 | A | 10/1997 | Breiner |

(Continued)

FOREIGN PATENT DOCUMENTS

| | | |
|---|---|---|
| CN | 1953657 A | 4/2007 |
| CN | 103393482 B | 4/2016 |

(Continued)

OTHER PUBLICATIONS

Badylak et al., Extracellular matrix as a biological scaffold material: Structure and function. Acta Biomater. Jan. 2009;5(1):1-13.

(Continued)

*Primary Examiner* — Suzette J Gherbi
(74) *Attorney, Agent, or Firm* — McCarter & English, LLP (57) ABSTRACT

Techniques and devices for improved breast surgeries are provided. The devices can include tissue matrix and synthetic meshes for surrounding breast implants or tissue expanders to provide improved implant outcomes for prepectoral implantation or other implantation techniques.

19 Claims, 5 Drawing Sheets

(56) References Cited

U.S. PATENT DOCUMENTS

| | | |
|---|---|---|
| 5,713,959 A | 2/1998 | Bartlett et al. |
| 5,733,337 A | 3/1998 | Carr, Jr. et al. |
| 5,755,791 A | 5/1998 | Whitson et al. |
| 5,779,734 A | 7/1998 | Ledergerber |
| 5,954,767 A | 9/1999 | Pajotin et al. |
| 5,968,096 A | 10/1999 | Whitson et al. |
| 5,997,575 A | 12/1999 | Whitson et al. |
| 6,051,648 A | 4/2000 | Rhee et al. |
| 6,075,180 A | 6/2000 | Sharber et al. |
| 6,099,566 A | 8/2000 | Vonderharr et al. |
| 6,203,570 B1 | 3/2001 | Baeke |
| 6,210,439 B1 | 4/2001 | Firmin et al. |
| 6,368,541 B1 | 4/2002 | Pajotin et al. |
| 6,638,308 B2 | 10/2003 | Corbitt, Jr. et al. |
| 6,666,892 B2 | 12/2003 | Hiles et al. |
| 6,723,133 B1 | 4/2004 | Pajotin |
| 6,736,823 B2 | 5/2004 | Darois et al. |
| 6,736,854 B2 | 5/2004 | Vadurro et al. |
| 6,740,122 B1 | 5/2004 | Pajotin |
| 6,777,231 B1 | 8/2004 | Katz et al. |
| 6,802,861 B1 | 10/2004 | Hamas |
| 7,011,688 B2 | 3/2006 | Gryska et al. |
| 7,081,135 B2 | 7/2006 | Smith et al. |
| 7,470,537 B2 | 12/2008 | Hedrick et al. |
| 7,476,249 B2 | 1/2009 | Frank |
| 7,651,684 B2 | 1/2010 | Hedrick et al. |
| 7,658,727 B1 | 2/2010 | Fernandes et al. |
| 7,699,895 B2 | 4/2010 | Hiles et al. |
| 7,875,074 B2 | 1/2011 | Chen et al. |
| 7,901,346 B2 | 3/2011 | Kovac et al. |
| 8,007,531 B2 | 8/2011 | Frank |
| 8,128,708 B2 | 3/2012 | Hiles et al. |
| 8,147,546 B2 | 4/2012 | Stone et al. |
| 8,192,486 B2 | 6/2012 | Glicksman |
| 8,198,408 B2 | 6/2012 | Huang |
| 8,313,527 B2 | 11/2012 | Powell et al. |
| 8,323,352 B2 | 12/2012 | Friedman et al. |
| 8,357,172 B2 | 1/2013 | Harper |
| 8,383,092 B2 | 2/2013 | Lee et al. |
| 8,487,012 B2 | 7/2013 | Goraltchouk et al. |
| 8,597,173 B2 | 12/2013 | O'Hern et al. |
| 8,685,296 B2 | 4/2014 | Liu et al. |
| 8,858,647 B2 | 10/2014 | Markman |
| 8,876,899 B2 | 11/2014 | Maxwell |
| 8,905,914 B2 | 12/2014 | Beckman et al. |
| 8,986,377 B2 | 3/2015 | Richter et al. |
| 9,101,458 B2 | 8/2015 | Sun et al. |
| 9,351,819 B2 | 5/2016 | Harper |
| 9,510,937 B2 | 12/2016 | Sun et al. |
| 9,549,812 B2 | 1/2017 | Shetty et al. |
| 10,004,590 B2 | 6/2018 | Shetty et al. |
| 10,039,633 B2 | 8/2018 | Ansorge et al. |
| 10,077,324 B2 | 9/2018 | Vail |
| 10,238,480 B2 | 3/2019 | Harper |
| 10,307,237 B2 * | 6/2019 | Wang .................. A61B 90/02 |
| 10,406,260 B2 | 9/2019 | Owens et al. |
| 10,449,034 B2 | 10/2019 | Bowley et al. |
| 10,695,165 B2 | 6/2020 | Shetty et al. |
| 2001/0041936 A1 | 11/2001 | Corbitt et al. |
| 2002/0103542 A1 | 8/2002 | Bilbo |
| 2002/0147461 A1 | 10/2002 | Aldrich et al. |
| 2003/0036803 A1 | 2/2003 | McGhan |
| 2003/0130747 A1 | 7/2003 | Abraham et al. |
| 2003/0212461 A1 | 11/2003 | Vadurro et al. |
| 2003/0212462 A1 | 11/2003 | Gryska et al. |
| 2003/0225355 A1 | 12/2003 | Butler |
| 2004/0049269 A1 | 3/2004 | Corbitt et al. |
| 2004/0260315 A1 | 12/2004 | Dell et al. |
| 2005/0021141 A1 | 1/2005 | Bleyer et al. |
| 2005/0025755 A1 | 2/2005 | Hedrick et al. |
| 2005/0119737 A1 | 6/2005 | Bene et al. |
| 2005/0165425 A1 | 7/2005 | Croce et al. |
| 2005/0187624 A1 | 8/2005 | Corbitt |
| 2005/0250977 A1 | 11/2005 | Montpetit et al. |
| 2005/0260176 A1 | 11/2005 | Ayares et al. |
| 2006/0030939 A1 | 2/2006 | Frank |
| 2006/0167338 A1 | 7/2006 | Shfaram |
| 2006/0206189 A1 | 9/2006 | Furst et al. |
| 2006/0264948 A1 | 11/2006 | Williams |
| 2007/0038299 A1 | 2/2007 | Stone et al. |
| 2007/0088299 A1 | 4/2007 | Ayre |
| 2007/0088434 A1 | 4/2007 | Frank |
| 2007/0116678 A1 | 5/2007 | Sung et al. |
| 2007/0250177 A1 | 10/2007 | Bilbo |
| 2008/0027273 A1 | 1/2008 | Gutterman |
| 2008/0082113 A1 | 4/2008 | Bishop et al. |
| 2008/0097601 A1 | 4/2008 | Codori-Hurff et al. |
| 2008/0108134 A1 | 5/2008 | Murphy et al. |
| 2008/0167729 A1 | 7/2008 | Nelson et al. |
| 2008/0241212 A1 | 10/2008 | Moses et al. |
| 2008/0260853 A1 | 10/2008 | Firestone |
| 2008/0281418 A1 | 11/2008 | Firestone |
| 2008/0281419 A1 | 11/2008 | Matheny et al. |
| 2009/0024227 A1 | 1/2009 | Lesh |
| 2009/0024228 A1 | 1/2009 | Lesh |
| 2009/0082864 A1 | 3/2009 | Chen et al. |
| 2009/0125107 A1 * | 5/2009 | Maxwell .................. A61L 27/50 |
| | | 623/8 |
| 2009/0198332 A1 | 8/2009 | Becker |
| 2009/0216338 A1 * | 8/2009 | Gingras ................ A61F 2/0077 |
| | | 623/23.72 |
| 2009/0240102 A1 | 9/2009 | Rane et al. |
| 2009/0240342 A1 | 9/2009 | Lindh, Sr. et al. |
| 2010/0003306 A1 | 1/2010 | Von Waldburg-Zeil |
| 2010/0010627 A1 | 1/2010 | Matheny |
| 2010/0023029 A1 | 1/2010 | Young |
| 2010/0028396 A1 | 2/2010 | Ward et al. |
| 2010/0152530 A1 | 6/2010 | Timmer et al. |
| 2010/0191330 A1 | 7/2010 | Lauryssen et al. |
| 2010/0217388 A1 | 8/2010 | Cohen et al. |
| 2010/0226960 A1 | 9/2010 | Chudzik et al. |
| 2010/0305696 A1 * | 12/2010 | Mao ........................ A61L 27/18 |
| | | 623/8 |
| 2011/0009960 A1 | 1/2011 | Altman et al. |
| 2011/0022171 A1 | 1/2011 | Richter et al. |
| 2011/0035004 A1 * | 2/2011 | Maxwell ................ A61L 27/362 |
| | | 623/8 |
| 2011/0082481 A1 | 4/2011 | Gingras et al. |
| 2011/0151011 A1 | 6/2011 | Flynn |
| 2011/0153017 A1 | 6/2011 | McClellan |
| 2011/0177150 A1 | 7/2011 | Pathak et al. |
| 2011/0190573 A1 | 8/2011 | Deegan |
| 2011/0196489 A1 | 8/2011 | Van Epps et al. |
| 2011/0257761 A1 * | 10/2011 | Mortarino ................ D04B 1/22 |
| | | 623/23.72 |
| 2011/0276039 A1 | 11/2011 | Markman |
| 2011/0293666 A1 | 12/2011 | Wang et al. |
| 2011/0293667 A1 | 12/2011 | Baksh et al. |
| 2011/0301706 A1 * | 12/2011 | Brooks ...................... A61F 2/12 |
| | | 623/8 |
| 2012/0052040 A1 | 3/2012 | Hunter et al. |
| 2012/0059411 A1 | 3/2012 | Sun et al. |
| 2012/0158134 A1 | 6/2012 | Codori-Hurff et al. |
| 2012/0165957 A1 | 6/2012 | Everland et al. |
| 2012/0255047 A1 | 10/2012 | Phelps et al. |
| 2012/0283826 A1 | 11/2012 | Moses et al. |
| 2013/0053956 A1 | 2/2013 | Powell et al. |
| 2013/0085579 A1 | 4/2013 | Markman |
| 2013/0224260 A1 | 8/2013 | Ward et al. |
| 2013/0273145 A1 | 10/2013 | Vail |
| 2013/0304098 A1 * | 11/2013 | Mortarino ............. A61F 2/0063 |
| | | 606/151 |
| 2014/0039617 A1 | 2/2014 | Maxwell |
| 2014/0088700 A1 | 3/2014 | Mortarino et al. |
| 2014/0141053 A1 | 5/2014 | Guillemette et al. |
| 2014/0257481 A1 * | 9/2014 | Brooks ...................... A61F 2/12 |
| | | 623/8 |
| 2014/0257482 A1 | 9/2014 | Ward et al. |
| 2014/0276993 A1 | 9/2014 | Reilly et al. |
| 2014/0276997 A1 | 9/2014 | Harrah et al. |
| 2015/0012089 A1 | 1/2015 | Shetty et al. |
| 2015/0112434 A1 | 4/2015 | Felix et al. |
| 2015/0119353 A1 | 4/2015 | Vail |

(56) References Cited

U.S. PATENT DOCUMENTS

| | | | |
|---|---|---|---|
| 2015/0150674 A1* | 6/2015 | Ansorge | A61F 2/12 623/8 |
| 2015/0223928 A1 | 8/2015 | Limem et al. | |
| 2015/0313708 A1 | 11/2015 | Mayo Martin | |
| 2015/0359622 A1 | 12/2015 | Matheny | |
| 2015/0359933 A1 | 12/2015 | Matheny | |
| 2015/0374830 A1 | 12/2015 | McKay | |
| 2016/0045198 A1 | 2/2016 | Bachrach | |
| 2016/0108144 A1 | 4/2016 | Vail | |
| 2016/0151062 A1 | 6/2016 | Bachrach | |
| 2016/0228235 A1 | 8/2016 | McQuillan et al. | |
| 2016/0256259 A1 | 9/2016 | Wirth et al. | |
| 2016/0324618 A1 | 11/2016 | Greenhalgh et al. | |
| 2016/0331504 A1* | 11/2016 | Wang | A61L 27/3666 |
| 2017/0007394 A1 | 1/2017 | Shetty et al. | |
| 2017/0027678 A1 | 2/2017 | Greenhalgh et al. | |
| 2017/0056157 A1 | 3/2017 | Hayzlett | |
| 2017/0065822 A1 | 3/2017 | Mashiach et al. | |
| 2017/0071723 A1 | 3/2017 | Sun et al. | |
| 2017/0100509 A1 | 4/2017 | Sun et al. | |
| 2017/0181841 A1 | 6/2017 | Weinzweig | |
| 2017/0216018 A1 | 8/2017 | Limem et al. | |
| 2017/0304488 A1 | 10/2017 | Levinson et al. | |
| 2017/0340437 A1 | 11/2017 | Bowley et al. | |
| 2018/0055624 A1 | 3/2018 | Re et al. | |
| 2018/0206978 A1 | 7/2018 | Rehnke | |
| 2018/0333252 A1 | 11/2018 | Ansorge et al. | |
| 2019/0247175 A1* | 8/2019 | Wang | A61F 2/0063 |
| 2021/0153997 A1* | 5/2021 | Limem | A61F 2/0077 |

FOREIGN PATENT DOCUMENTS

| | | |
|---|---|---|
| DE | 102006029605 A1 | 12/2007 |
| EP | 0338701 A2 | 10/1989 |
| FR | 2447182 B1 | 7/1983 |
| FR | 2682284 A1 | 4/1993 |
| FR | 2746298 A1 | 9/1997 |
| JP | H09-47503 A | 2/1997 |
| JP | H10-158906 | 6/1998 |
| JP | 2005-536228 A | 12/2005 |
| JP | 2013-500062 A | 1/2013 |
| WO | WO-2003/068118 A1 | 8/2003 |
| WO | WO-2003/084410 A1 | 10/2003 |
| WO | WO-2004/096098 A1 | 11/2004 |
| WO | WO-2005/089411 A2 | 9/2005 |
| WO | WO-2006/115892 A2 | 11/2006 |
| WO | WO-2006/135998 A2 | 12/2006 |
| WO | WO-2007/004214 A2 | 1/2007 |
| WO | WO-2007/131110 A2 | 11/2007 |
| WO | WO-2007/134134 A2 | 11/2007 |
| WO | WO-2008/016919 A2 | 2/2008 |
| WO | WO-2008/067317 A2 | 6/2008 |
| WO | WO-2008/121816 A2 | 10/2008 |
| WO | WO-2009/001293 A1 | 12/2008 |
| WO | WO-2009/065013 A1 | 5/2009 |
| WO | WO-2009/114052 A2 | 9/2009 |
| WO | WO-2010/041101 A1 | 4/2010 |
| WO | WO-2011/063412 A2 | 5/2011 |
| WO | WO-2013/106556 A2 | 7/2013 |
| WO | WO-2014/041577 A1 | 3/2014 |
| WO | WO-2015/006737 A1 | 1/2015 |
| WO | WO-2015/065923 A1 | 5/2015 |

OTHER PUBLICATIONS

Baxter, Intracapsular allogenic dermal grafts for breast implant-related problems. Blast Reconstr Surg. Nov. 2003;112(6):1692-6.

Berna et al., Evaluation of a novel breast reconstruction technique using the Braxon(@) acellular dermal matrix: a new muscle-sparing breast reconstruction. ANZ J Surg. Jun. 2017;87(6):493-498.

Bindingnavele et al., Use of acellular cadaveric dermis and tissue expansion in postmastectomy breast reconstruction. J Blast Reconstr Aesthet Surg. 2007;60(11):1214-8.

Blackburn et al., Negative-pressure dressings as a bolster for skin grafts. Ann Blast Surg. May 1998;40(5):453-7.

Breuing et al., Immediate bilateral breast reconstruction with implants and inferolateral AlloDerm slings. Ann Blast Surg. Sep. 2005;55(3):232-9.

Breuing et al., Inferolateral AlloDerm hammock for implant coverage in breast reconstruction. Ann Blast Surg. Sep. 2007;59(3):250-5.

Colwell et al., Improving shape and symmetry in mastopexy with autologous or cadaveric dermal slings. Ann Blast Surg. Aug. 2008;61(2):138-42.

Darcy, A technique for preparing meshed skin grafts with planned expansion ratios. Br J Blast Surg. Jan. 2003;56(1):77-9.

Duncan, Correction of implant rippling using allograft dermis. Aesthet Surg J. Jan. 2001;21(1):81-4.

Gamboa-Bobadilla, Implant breast reconstruction using acellular dermal matrix. Ann Blast Surg. Jan. 2006;56(1):22-5.

Góes et al., The application of mesh support in periareolar breast surgery: clinical and mammographic evaluation. Aesthetic Blast Surg. Sep.-Oct. 2004;28(5):268-74.

Góes, Beriareolar Mammaplasty with Mixed Mesh Support: The Double Skin Technique. Operative Techniques in Blastic and Reconstructive Surgery. Aug. 1996;3(3):199-206.

Góes, Periareolar mammaplasty: double skin technique with application of polyglactine or mixed mesh. Blast Reconstr Surg. Apr. 1996;97(5):959-68.

Góes, Periareolar Mammaplasty: Double Skin Technique with Appliction of Polygractine 910 Mesh. Rev. Soc. Bras. Cir. Blast. Estet. Reconstr. Jan./Dec. 1992;7(1,2,3):1-5.

Góes, Periareolar Mastopexy and Reduction with Mesh Support, Double Skin Technique. Surgery of the Breast: Principles and Art. Scott L. Spear (Ed.), Lippincott-Raven Rublishers, Philadelphia. Chapter 51, pp. 697-708 (1998).

Góes, Periareolar Mastopexy: Double Skin Techique with Mess Support. Aesthetic Surgery Journal. Mar.-Apr. 2003;23:129-135.

Pope, Mesh Skin Grafting. Veterinary Clinics of North America: Small Animal Bractice. Jan. 1990;20(1):177-187.

Salzberg, Nonexpansive immediate breast reconstruction using human acellular tissue matrix graft (AlloDerm). Ann Blast Surg. Jul. 2006;57(1):1-5.

Topol et al., Immediate single-stage breast reconstruction using implants and human acellular dermal tissue matrix with adjustment of the lower pole of the breast to reduce unwanted lift. Ann Blast Surg. Nov. 2008;61(5):494-9.

Xu et al., A porcine-derived acellular dermal scaffold that supports soft tissue regeneration: removal of terminal galactose-alpha-(1,3)-galactose and retention of matrix structure. Tissue Eng Part A. Jul. 2009;15(7):1807-19.

Zienowicz et al., Implant-based breast reconstruction with allograft. Plast Reconstr Surg. Aug. 2007;120(2):373-81.

U.S. Appl. No. 14/371,291, filed Jul. 9, 2017, U.S. Pat. No. 9,549,812, Issued.

U.S. Appl. No. 15/271,644, filed Sep. 21, 2016, U.S. Pat. No. 10,004,590, Issued.

U.S. Appl. No. 16/000,158, filed Jun. 5, 2018, U.S. Pat. No. 10,695,165, Issued.

U.S. Appl. No. 16/881,487, filed May 22, 2020, Pending.

U.S. Appl. No. 14/406,263, filed Dec. 8, 2014, U.S. Pat. No. 10,039,633, Issued.

U.S. Appl. No. 16/049,089, filed Jul. 30, 2018, 2018-0333252, Published.

U.S. Appl. No. 15/139,458, filed Apr. 7, 2016, U.S. Pat. No. 10,307,237, Issued.

U.S. Appl. No. 16/388,966, filed Apr. 19, 2019, 2019-0247175, Published.

U.S. Appl. No. 16/842,162, filed Apr. 7, 2020, Pending.

* cited by examiner

BREAST TREATMENT DEVICE

The present disclosure claims priority under 35 USC § 119 to U.S. Provisional Application 62/842,915, which was filed on May 3, 2019 and is herein incorporated by reference.

The present disclosure relates generally to devices for improving breast surgeries, including implants or tissue expanders incorporating synthetic meshes or acellular tissue matrices.

Currently, during some surgical breast procedures, surgeons must suture tissue matrix along an inframammary fold, release muscle tissue from its insertion at the sternum, place a tissue expander (or permanent implant) in a desired position within the breast, and suture the tissue matrix along the edge of the released muscle. These procedures can be time consuming and require skill to achieve desired outcomes. Post operatively, patients may experience pain related to the release of the muscle. Often the muscle heals to the skin flap, which causes the implants to displace when the muscle is activated, thereby causing deformities.

The present disclosure provides surgeons with a tool and technique to manipulate and position implants and tissue matrix within the breast pocket to achieve the desired outcome using less tissue manipulation (e.g., without release of muscle).

In various embodiments, a method for treatment of a breast is disclosed herein. The method comprises selecting a breast implant or tissue expander, selecting a synthetic mesh, selecting a layer of acellular tissue matrix, applying the synthetic mesh to a posterior portion of the breast implant or tissue expander, applying the acellular tissue matrix to an anterior portion of the breast implant or tissue expander, securing the synthetic mesh to the acellular tissue matrix, and implanting the breast implant or tissue expander in an implantation site.

In various embodiments, a breast treatment device is provided. The device comprises a synthetic mesh comprising at least one securing means for securing the synthetic mesh to an implant or tissue expander and a layer of acellular tissue matrix comprising at least one receiving means for attaching the layer of acellular tissue matrix to the implant or tissue expander, wherein the at least one receiving means is configured to receive the securing means, and wherein the device is secured in an implantation site.

In certain embodiments, a breast treatment device is provided. The device can comprise a synthetic mesh, wherein the synthetic mesh comprises at least two straps, wherein the at least two straps are configured to secure the device to a breast implant or tissue expander. The device can further comprise a layer of acellular tissue matrix, wherein the acellular tissue matrix comprises at least two holes sized and shaped to receive the two straps.

In certain embodiments, a breast treatment device is provided. The device can comprise a breast implant or tissue expander, a synthetic mesh comprising at least one strap, and a layer of acellular tissue matrix, wherein the synthetic mesh comprises at least one strap and the acellular tissue matrix comprises at least one hole, and the at least one strap and at least one hole are configured to secure the layer of acellular tissue matrix to an anterior portion of the breast implant or tissue expander and the synthetic mesh to a posterior portion of the breast implant or tissue expander.

In various embodiments, a breast treatment device is provided. The device comprises a breast implant or tissue expander and a synthetic mesh shaped as a clamshell and configured to surround the breast implant or tissue expander.

In various embodiments, a flexible synthetic mesh for breast treatment is provided. The mesh comprises a first section of flexible material having a rounded outer border, a second section of flexible material having a rounded outer border, a joining section connecting the first section and second section such that the first section and second section can be folded into a clamshell configuration, a first elongated section of material and a second elongated section of material each extending from a distal end of the first section of flexible material, a first hole near a distal end of the second section of flexible material sized and shaped to receive an end portion of the first elongated section of material; and a second hole near a distal end of the second section of flexible material sized and shaped to receive an end portion of the second elongated section of material.

In various embodiments, a method for treatment of a breast is disclosed herein. The method comprises selecting a breast implant or tissue expander, selecting a synthetic mesh shaped as a clamshell, applying one portion of the clamshell of the synthetic mesh to a posterior portion of the breast implant or tissue expander, applying another portion of the clamshell of the synthetic mesh to an anterior portion the breast implant or tissue expander, securing the synthetic mesh to the breast implant or tissue expander; and implanting the breast implant or tissue expander in an implantation site.

DESCRIPTION OF EXEMPLARY EMBODIMENTS

Reference will now be made in detail to various embodiments of the disclosed devices and methods, examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Any range described herein will be understood to include the endpoints and all values between the endpoints.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

The terms "breast implant" and "implant," as used herein, generally refer to medical devices that are implanted either under muscle or under or within breast tissue or above the chest muscle for breast augmentation or reconstruction. Such implants can include saline filled or silicone gel implants, or other implants that provide volume for breast augmentation. The terms "breast tissue expander," "tissue expander," and "expander," as used herein, generally refer to devices that are implanted within breast or other tissue or muscle, and which are expanded over time to stretch breast or other tissue and skin. The tissue expander can be made from any biocompatible and/or non-reactive material commonly used in implantable medical devices such as standard tissue expanders or breast implants.

As previously mentioned, the present disclosure provides improved methods and devices for manipulating and implanting breast implants or tissue expanders. Devices and methods can allow for pre-pectoral implantation of an implant or expander, and/or can allow manipulation of the implant or expander, including, for example, controlling the shape, position, or projection of the implant or expander.

Figure 1:
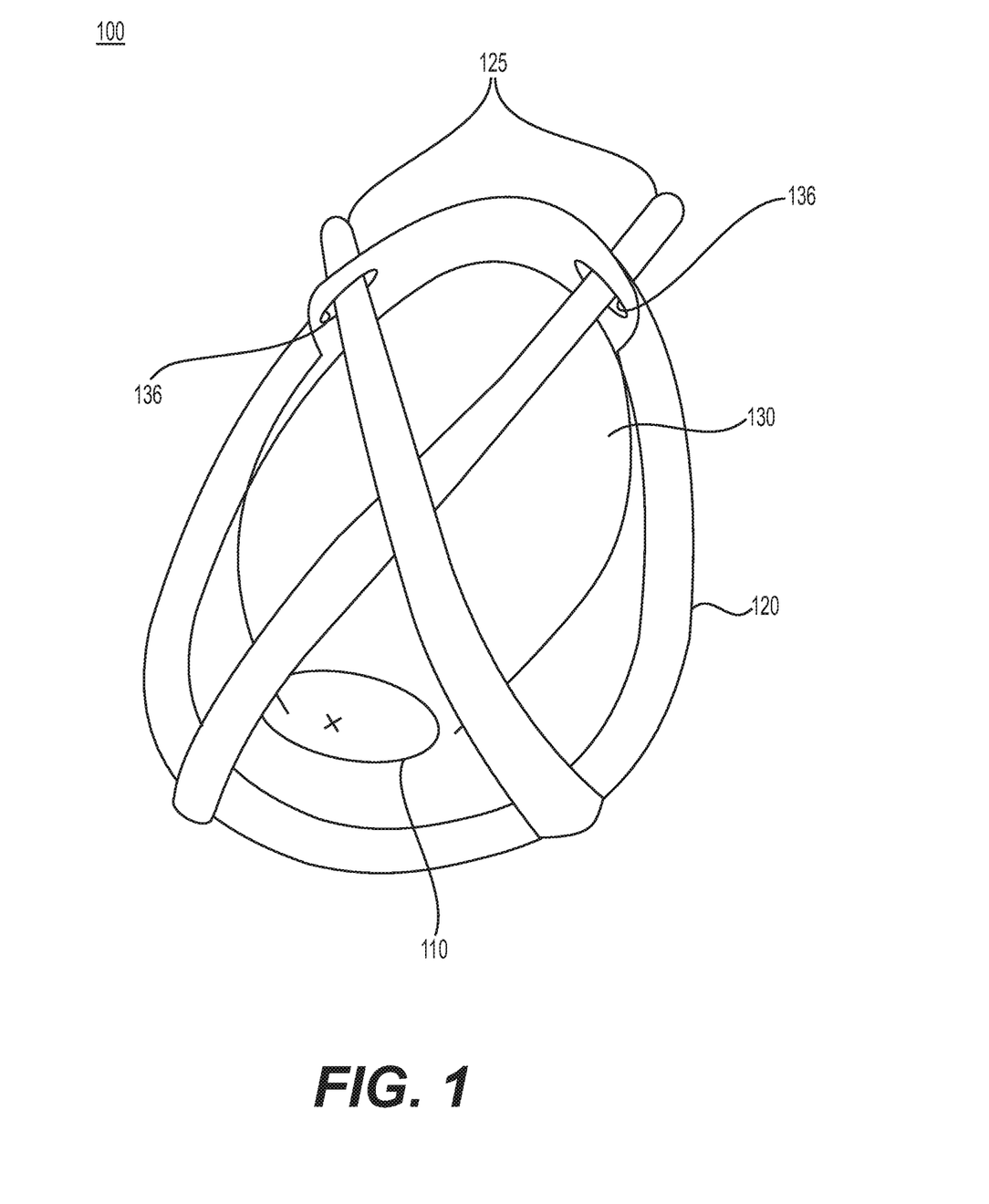
FIG. 1 is an anterior view of a breast treatment device according to various embodiments.

FIG. 1 is an anterior view of a breast treatment device 100 according to various embodiments. The device 100 can comprise a synthetic mesh 120 comprising at least one securing means 125 (e.g., a strap or elongated portion) for securing the synthetic mesh 120 to an implant 110 or tissue expander. The device 100 can further comprise an a layer of acellular tissue matrix 130 comprising at least one receiving means 138 (e.g., or hole or opening) for attaching the layer of acellular tissue matrix to the implant 110 or tissue expander.

The synthetic mesh 120 material used to produce the devices described herein may be formed of a variety of suitable materials. Such suitable materials may include polymers. In an embodiment, the synthetic mesh is formed of polyglicoic acid. In a further embodiment, the synthetic mesh is formed of polyglactin 910. In yet a further embodiment, the synthetic mesh is formed of Vicryl®, produced by ETHICON® CORPORATION.

The tissue matrix 130 can also be formed of a variety of suitable materials. For example, suitable tissue matrices include ALLODERM® and STRATTICE®, which are human and porcine acellular dermal matrices produced by LIFECELL® CORPORATION. Alternatively, other suitable acellular tissue matrices can be used. For example, a number of biological scaffold materials as described by Badylak et al., or any other similar materials, can be used to produce tissues with a stable three-dimensional shape. Badylak et al., "Extracellular Matrix as a Biological Scaffold Material: Structure and Function," *Acta Biomaterialia* (2008), doi: 10.1016/j.actbio.2008.09.013. Any FDA approved surgical mesh or similar human tissue product, including biologic, synthetic, or hybrid materials may be used. The tissue matrix 130 may be a layer or any other suitable configuration for providing sufficient support to the implant or expander, such as multiple layers, a mesh, or a pad.

Figure 2:
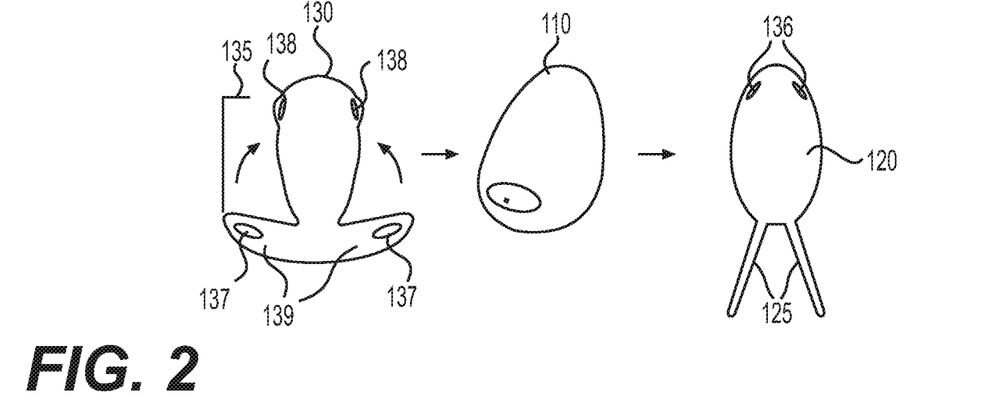
FIG. 2 is an anterior view of components of a breast treatment device according to various embodiments.
Figure 3:
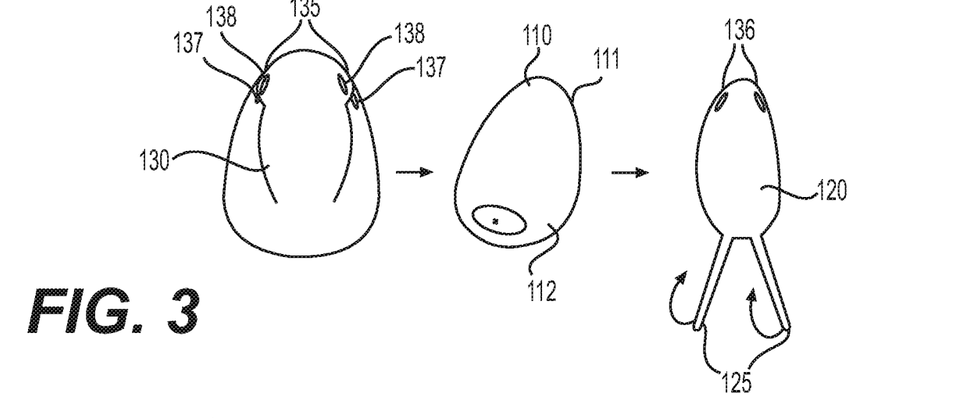
FIG. 3 is an posterior view of components of a breast treatment device according to various embodiments.
Figure 4A:
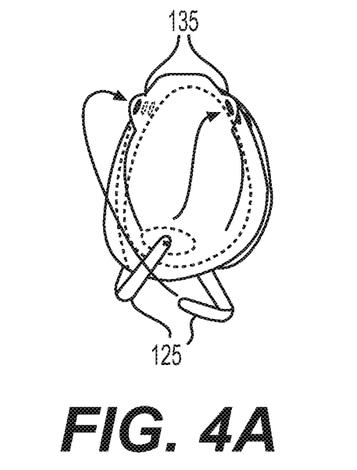
FIG. 4A is a posterior view of a layer of acellular tissue matrix, a breast implant, and a synthetic mesh, according to various embodiments.
Figure 4B:
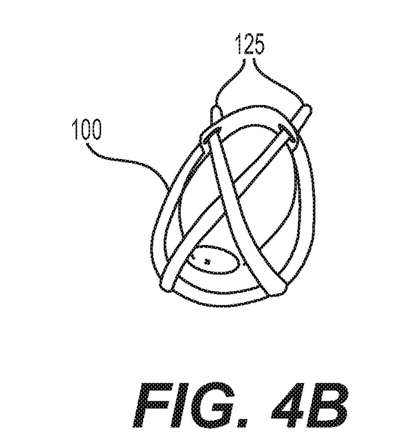
FIG. 4B is a anterior view of a layer of acellular tissue matrix, a breast implant, and a synthetic mesh, according to various embodiments.

The device 100 can be understood with reference to its components, which may be considered together or individually within the scope of the present inventions. To more fully understand the disclosed devices and methods additional views of the components and assembled parts are discussed. FIG. 2 is an anterior view of components of a breast treatment device according to various embodiments. FIG. 3 is a posterior view of components of a breast treatment device according to various embodiments. FIG. 4A is a posterior view of a layer of acellular tissue matrix, a securable breast implant, and a synthetic mesh, according to various embodiments; and FIG. 4B is an anterior view of a layer of acellular tissue matrix, a securable breast implant, and a synthetic mesh, according to various embodiments.

As shown, the synthetic mesh 120 comprises at least two straps 125, which can be used to attach the mesh 120 to the tissue matrix 130. In one embodiment, the mesh 120 is attached to the tissue matrix 130 by passing the straps 125 through holes 136 at a distal end of the mesh 120, and/or holes 137, 138 in the tissue matrix 130.

In some cases, the mesh 120 and tissue matrix 130 are provided with or intended to be used with an implant or tissue expander. The mesh 120 and tissue matrix 130 can be sold, packaged, or used together or individually, or along with an implant or tissue expander 110.

In some cases, the tissue matrix 130 is formed with a top portion 135 and bottom portion 139. The top portion 135 can include an elongated and at least partially rounded border and can include holes 138 at a distal end for receiving portions of the straps 125. The bottom portion 139 can include two sections extending laterally from the top portion 135, and optionally including additional openings 137. The bottom portion 139 can be folded upward (See FIG. 3), thereby forming a cup shaped region or pocket that can be made to conform to an anterior surface of an implant or tissue expander 110.

FIGS. 4A and 4B illustrate how the synthetic mesh 120 and tissue matrix 130 can be secured to one another and around an implant or tissue expander 110. In various embodiments, the synthetic mesh 120 is applied to a posterior portion 111 of the breast implant or tissue expander 110, and the tissue matrix 130 is applied to an anterior portion 112 of the breast implant or tissue expander 110. Further, as discussed in more detail below, the implant or tissue expander 110, along with a secured mesh 120 and tissue matrix 130 can be implanted within a breast.

Figure 5:
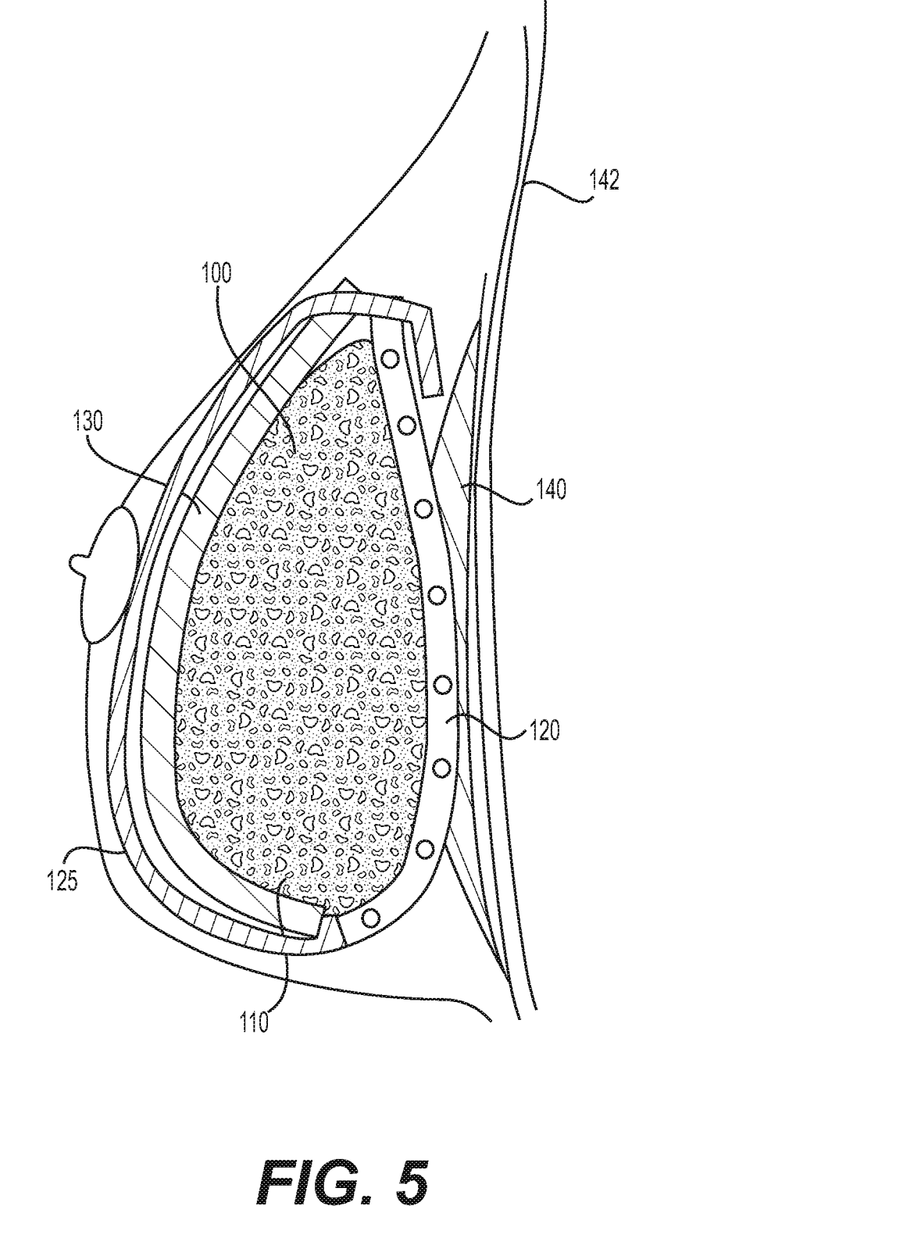
FIG. 5 is a side, cut away view of a breast implant implanted subcutaneously and anterior to pectoral muscle and incorporating the synthetic mesh and tissue matrix, according to various embodiments.

FIG. 5 is a side, cut away view of a breast implant 110 implanted subcutaneously and anterior to pectoral muscle 140 and incorporating the synthetic mesh 120 and tissue matrix 130, according to various embodiments.

As shown, the implant 110 is anterior to a pectoralis muscle 140. And although a pre-pectoral position, as shown, may be preferred in some cases, it should be appreciated that the present devices and methods can be used in a variety of procedures and anatomic locations.

After or during implantation, the synthetic mesh 120 or tissue matrix 130 may assist in securing the implant or expander 110 in place. For example, the synthetic mesh 120 may be secured to portions of the chest wall 142 or other appropriate tissue to help position and maintain the implant or expander 110. Further, the tissue matrix 130, positioned an anterior to a portion of the implant or expander 110, can provide an interface between overlying skin or subcutaneous tissues. Accordingly, the tissue matrix 130 can provide a number of functions, including supporting the implant or expander, providing a material for more rapid or better vascularization, tissue regeneration, and ingrowth, prevention or reduction of scar formation and/or contracture, and/or providing additional tissue to prevent rippling, bottoming out, or any other undesired aesthetic or reconstructive result.

The structure of the combination of the mesh 120 and tissue matrix 130 can also allow manipulation and better implant control. For example, the strap(s) 125 may be adjusted to vary or alter a projection and/or position of the implant or expander, thereby improving a final implant result.

Figure 6:
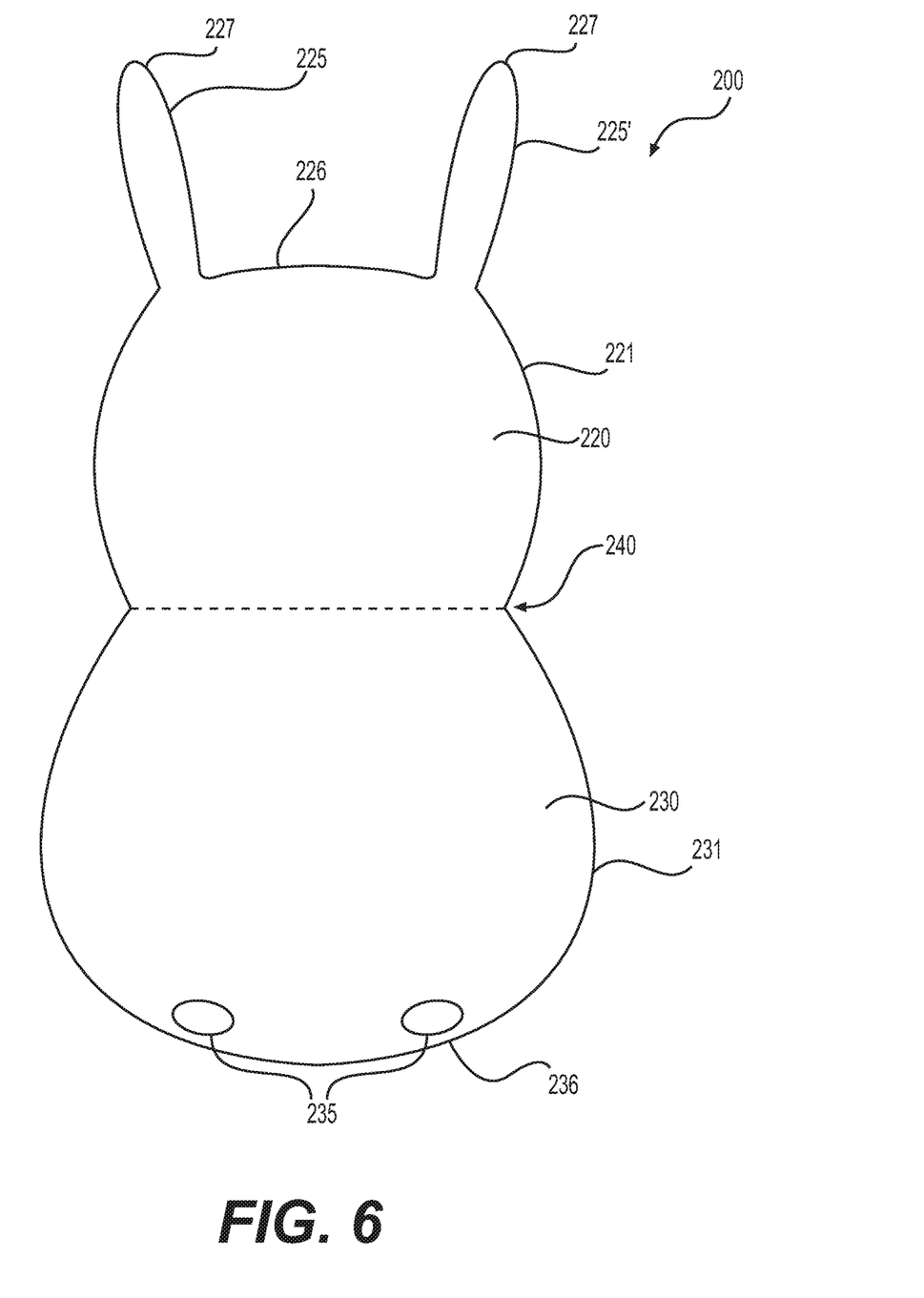
FIG. 6 is a perspective view of a synthetic mesh in an open configuration before being attached to a breast implant or tissue matrix according to certain exemplary embodiments.

As described previously, the devices 100 include both a synthetic and tissue matrix component, but in other embodiments, the disclosed devices and methods may incorporate a single synthetic material. For example, FIG. 6 is a perspective view of a synthetic mesh 200, which can be used with methods similar to those discussed above. As shown, the device 200 is in an open configuration before being attached to a breast implant or tissue matrix according to certain exemplary embodiments.

As with the material used to produce the mesh 120, the synthetic mesh 120 may be formed of a variety of suitable materials. Such suitable materials may include polymers. In an embodiment, the synthetic mesh is formed of polyglicoic acid. In a further embodiment, the synthetic mesh is formed of polyglactin 910. In yet a further embodiment, the synthetic mesh is formed of Vicryl®, produced by ETHICON® CORPORATION.

The device 200 can include a flexible synthetic mesh 200 that comprises a first section 220 of flexible material having a rounded outer border 221 and a second section 230 of flexible material having a rounded outer border 231.

The first section 220 and second section 230 can be connected at a joining section 240. As such, the device 200 comprises a single sheet of material that, when flexible, can be folded into a clamshell configuration to cover an implant or tissue expander 110.

The device 200 can further comprise a first elongated section of material 225 and a second elongated section of material 225' each extending from a distal end 226 of the first section 220 of flexible material as well as at least one hole 235 near a distal end 236. The hole(s) 235 are sized and shaped to receive an end portion 227, 227' and the elongated sections of material 225, 225'.

Figure 7:
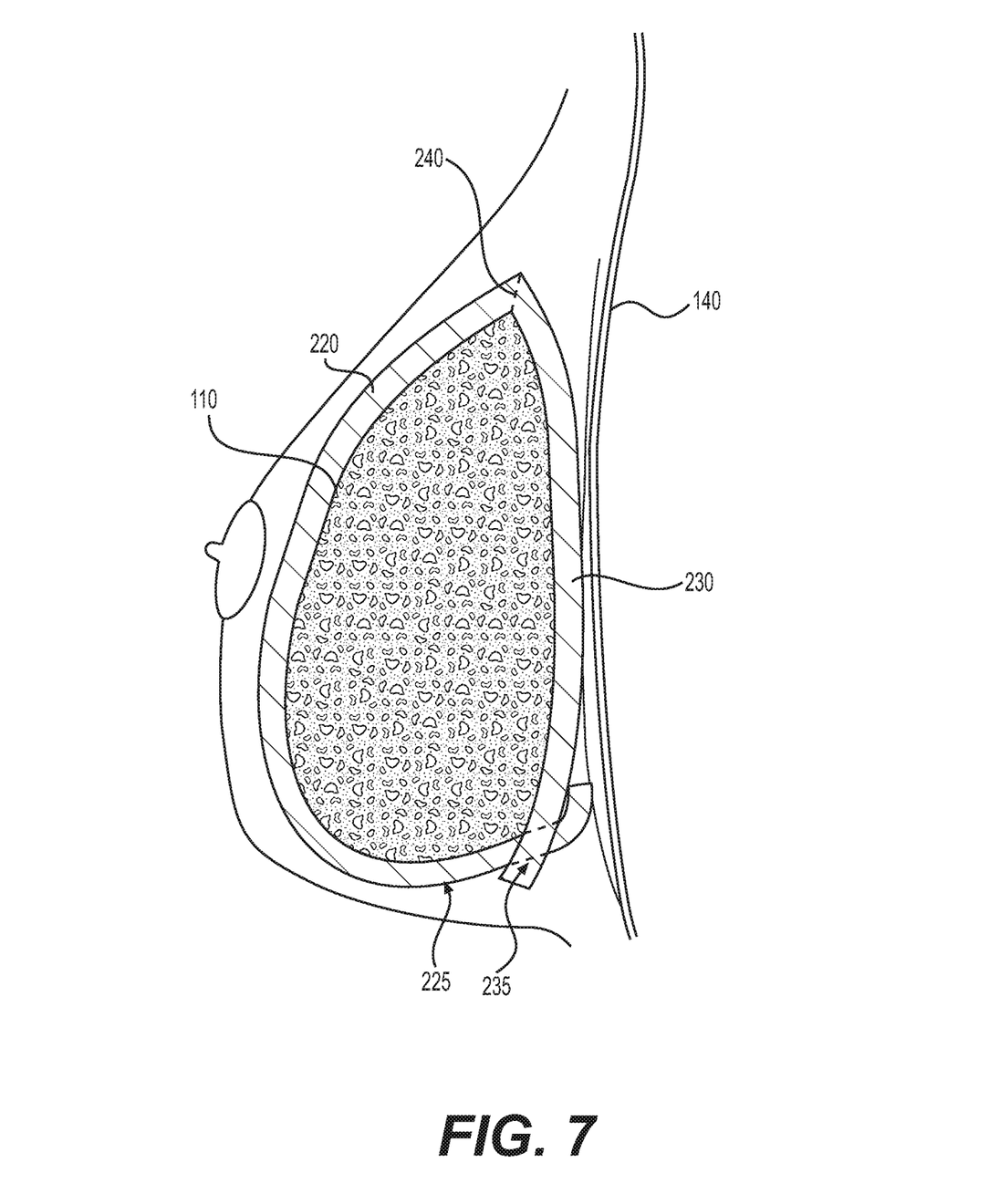
FIG. 7 is a side, cut away view of a breast implant implanted subcutaneously and anterior to pectoral muscle and incorporating the synthetic mesh, according to various embodiments.

Similar to the devices described with respect to FIGS. 1-4, the device 200 can be placed around an implant or tissue expander 110 and implanted within a breast. FIG. 7 is a side, cut away view of a breast implant implanted subcutaneously and anterior to pectoral muscle and incorporating the synthetic mesh, according to various embodiments.

As with the devices described previously, the device 200 provides a number of potential advantages. For example, the synthetic mesh 200 can assist in securing the implant or expander 110 in place. For example, the synthetic mesh 200 may be secured to portions of the chest wall 140 or other appropriate tissue to help position and maintain the implant or expander 110. The structure of the combination of the mesh 120 and tissue matrix 130 can also allow manipulation and better implant control. For example, the strap(s) 125 may be adjusted to vary or alter a projection and/or position of the implant or expander, thereby improving a final implant result.

Other embodiments will be apparent to those skilled in the art from consideration of the specification and practice of this disclosure. It is intended that the specification and examples be considered as exemplary only, with the true scope and spirit of the disclosed devices and methods being indicated by the following claims.

What is claimed is:

1. A method for treatment of a breast, comprising:
   selecting a breast implant or tissue expander;
   selecting a synthetic mesh;
   selecting a layer of acellular tissue matrix;
   applying the synthetic mesh to a posterior portion of the breast implant or tissue expander;
   applying the acellular tissue matrix to an anterior portion the breast implant or tissue expander;
   securing the synthetic mesh to the acellular tissue matrix; and
   implanting the breast implant or tissue expander in an implantation site, wherein the synthetic mesh and the acellular tissue matrix are secured to the breast implant or tissue expander by inserting at least one strap attached to the synthetic mesh through at least one hole in the acellular tissue matrix.

2. The method of claim 1, further comprising:
   adjusting a position and a projection of the breast implant or tissue expander in the implantation site.

3. The method of claim 2, wherein the position and the projection of the breast implant or tissue expander in the implantation site are adjusted by manipulating the at least one strap attached to the synthetic mesh.

4. The method of claim 1, further comprising securing the breast implant or tissue expander in the implantation site.

5. The method of claim 1, wherein the breast implant or tissue expander is implanted anterior to a pectoral muscle.

6. The method of claim 1, wherein the synthetic mesh comprises polyglycolic acid.

7. The method of claim 6, wherein the synthetic mesh comprises polyglactin 910.

8. The method of claim 1, wherein the acellular tissue matrix comprises a dermal acellular tissue matrix.

9. The method of claim 1, wherein after inserting the at least one strap, a position and a projection of the synthetic mesh and the acellular tissue matrix are adjusted in the implantation site by manipulating the at least one strap.

10. The method of claim 1, wherein the at least one strap is inserted through at least one hole in the synthetic mesh.

11. The method of claim 10, wherein the at least one hole in the synthetic mesh is adjacent to the at least one hole in the acellular tissue matrix.

12. A device for breast treatment, comprising:
    a breast implant or tissue expander;
    a synthetic mesh comprising at least one strap; and
    a layer of acellular tissue matrix, wherein the synthetic mesh comprises at least one strap and the acellular tissue matrix comprises at least one hole, and the at least one strap and at least one hole are configured to secure the layer of acellular tissue matrix to an anterior portion of the breast implant or tissue expander and the synthetic mesh to a posterior portion of the breast implant or tissue expander.

13. The device of claim 12, wherein the synthetic mesh comprises polyglycolic acid.

14. The device of claim 13, wherein the synthetic mesh comprises polyglactin 910.

15. The device of claim 12, wherein the acellular tissue matrix comprises a dermal acellular tissue matrix.

16. The device of claim 12, wherein the at least one strap allows adjustment of a position and a projection of the breast implant or tissue expander in an implantation site.

17. The device of claim 16, wherein the at least one strap is inserted through the hole in the acellular tissue matrix.

18. The device of claim 12, wherein the synthetic mesh is configured to be secured to tissue in an implantation site.

19. The device of claim 12, wherein the synthetic mesh comprises at least two straps.

* * * * *

UNITED STATES PATENT AND TRADEMARK OFFICE
CERTIFICATE OF CORRECTION

PATENT NO. : 11,298,220 B2
APPLICATION NO. : 16/864670
DATED : April 12, 2022
INVENTOR(S) : Kai-Roy Wang et al.

It is certified that error appears in the above-identified patent and that said Letters Patent is hereby corrected as shown below:

On the Title Page

Page 3, item [56], Column 1, Line 25, replace "Re" with --Barere--.

Page 3, item [56], Column 1, Line 2 of Other Publications, replace "Blast" with --Plast--.

Page 3, item [56], Column 1, Line 4 of Other Publications, replace "Braxon(@)" with --Braxon(®)--.

Page 3, item [56], Column 2, Line 2, replace "Blast" with --Plast--.

Page 3, item [56], Column 2, Line 5, replace "Blast" with --Plast--.

Page 3, item [56], Column 2, Line 7, replace "Blast" with --Plast--.

Page 3, item [56], Column 2, Line 10, replace "Blast" with --Plast--.

Page 3, item [56], Column 2, Line 13, replace "Blast" with --Plast--.

Page 3, item [56], Column 2, Line 16, replace "Blast" with --Plast--.

Page 3, item [56], Column 2, Line 20, replace "Blast" with --Plast--.

Page 3, item [56], Column 2, Line 22, replace "Blast" with --Plast--.

Page 3, item [56], Column 2, Line 24, replace "Beriareolar" with --Periareolar--.

Page 3, item [56], Column 2, Line 25, replace "Blastic" with --Plastic--.

Page 3, item [56], Column 2, Line 28, replace "polyglactine" with --polyglactin--.

Signed and Sealed this
Fourteenth Day of June, 2022

Katherine Kelly Vidal
*Director of the United States Patent and Trademark Office*

CERTIFICATE OF CORRECTION (continued)
U.S. Pat. No. 11,298,220 B2

Page 3, item [56], Column 2, Line 30-31, replace "Appliction" with --Application--.

Page 3, item [56], Column 2, Line 31, replace "Polygractine" with --Polyglactin--.

Page 3, item [56], Column 2, Line 31, replace "Blast" with --Plast--.

Page 3, item [56], Column 2, Line 36, replace "Rublishers" with --Publishers--.

Page 3, item [56], Column 2, Line 37, replace "Techique" with --Technique--.

Page 3, item [56], Column 2, Line 40, replace "Bractice" with --Practice--.

Page 3, item [56], Column 2, Line 42, replace "Blast" with --Plast--.

Page 3, item [56], Column 2, Line 46, replace "Blast" with --Plast--.

Page 3, item [56], Column 2, Line 65, replace "Apr. 7" with --Apr. 27--.

In the Specification

Column 2, Line 22, insert --of-- after --portion--.

Column 3, Line 36, replace "an a" with --a--.

Column 3, Line 45, replace "polyglicoic" with --polyglycolic--.

Column 5, Line 22, replace "polyglicoic" with --polyglycolic--.

In the Claims

Column 6, Claim 1, Line 8, insert --of-- after --portion--.